(12) United States Patent
Seib et al.

(10) Patent No.: US 6,299,907 B1
(45) Date of Patent: *Oct. 9, 2001

(54) REVERSIBLY SWELLABLE STARCH PRODUCTS

(75) Inventors: Paul A. Seib; Kyungsoo Woo, both of Manhattan, KS (US)

(73) Assignee: Kansas State University Research Foundation, Manhattan, KS (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/096,990

(22) Filed: Jun. 12, 1998

(51) Int. Cl.[7] .................. A61K 9/50; A61K 9/14; A61K 47/00; A61K 6/00; A21D 10/00
(52) U.S. Cl. ............ 424/499; 424/489; 424/439; 424/401; 426/549; 426/94; 426/578
(58) Field of Search .................. 424/489, 464, 424/465, 468, 488, 405, 66; 127/71, 33; 426/549

(56) References Cited

U.S. PATENT DOCUMENTS

| | | |
|---|---|---|
| 2,626,257 | 1/1953 | Caldwell et al. . |
| 2,801,242 | 7/1957 | Kerr et al. . |
| 2,852,393 | 9/1958 | Kerr et al. . |
| 4,183,969 | 1/1980 | Rubens . |
| 4,219,646 | 8/1980 | Rubens . |
| 4,491,483 * | 1/1985 | Dudacek et al. ............ 127/33 |
| 5,019,375 * | 5/1991 | Tanner et al. ............. 424/66 |
| 5,593,503 * | 1/1997 | Shi et al. . |
| 5,837,273 * | 11/1998 | Shasha et al. . |
| 5,855,946 * | 1/1999 | Seib et al. .............. 426/549 |
| 5,879,707 * | 3/1999 | Cartilier et al. ........... 424/468 |

OTHER PUBLICATIONS

Englyst et al.; Classification and measurement of nutritionally important starch fractions; European J. Clin. Nutrition; 45:533–550 (Suppl. 2) (1992).

Ranhotra et al.; Effect of Resistant Starch on Blood and Liver Lipids in Hamsters; Cereal Chem.; 73(2):176–178 (1996).

Eerlingen et al.; Enzyme–Resistant Starch. I. Quantitative and Qualitative Influence of Incubation Time and Temperature of Autoclaved Starch on Resistant Starch Formation; Cereal Chem.; 70(3):339–344 (1993).

Extrusion Communique/Jul./Aug. 1996; IE Ingredients Extra—National Starch and APV find high–fibre extrusion success.

Sievert et al.; Enzyme–Resistant Starch. I. Characterization and Evaluation by Enzymatic, Thermoanalytical, and Microscopic Methods; Cereal Chem.; 66(4):342–347 (1989).

Janzen; Verdaulichkeit von Stärken und phosphatierten Stärken mittels Pankreatin; Die Stärke; No. 9/21. Jahrg. (1966).

English Translation of Janzen Article; Die Starke, No. 9/21, Jahrg. (1966).

* cited by examiner

*Primary Examiner*—Thurman K. Page
*Assistant Examiner*—Robert M. Joynes
(74) *Attorney, Agent, or Firm*—Hovey, Williams, Timmons & Collins

(57) ABSTRACT

Reversible swellable modified starch products are provided in the form of individual, chemically cross-linked starch granules capable of undergoing multiple hot or cold water swelling/drying cycles without losing the individuality of the starch granules, and with essentially no loss of starch solubles. The starches are prepared by forming a dispersion of starch granules in water, with the granules undergoing swelling and having a crystalline phase; a cross-linker (preferably a phosphorylating agent) is added to the dispersion in order to cross-link the starch under conditions to avoid complete gelatinization thereof. The swollen/cross-linked starch granules are then heated in excess water in order to melt the crystalline phase of the granules. The granules exhibit a network-like structure with internal voids.

62 Claims, 11 Drawing Sheets

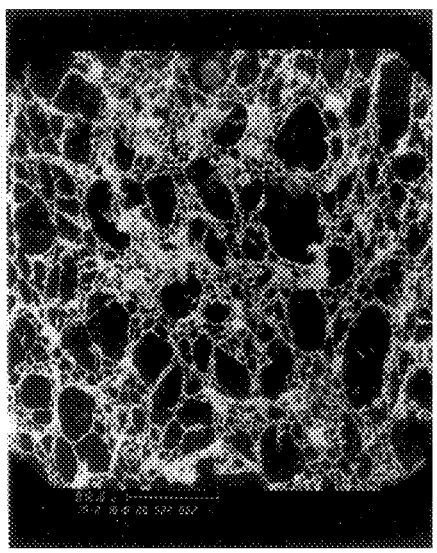 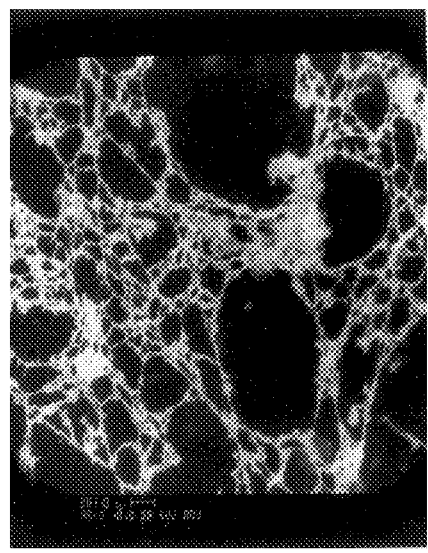
Fig. 3                    Fig. 4

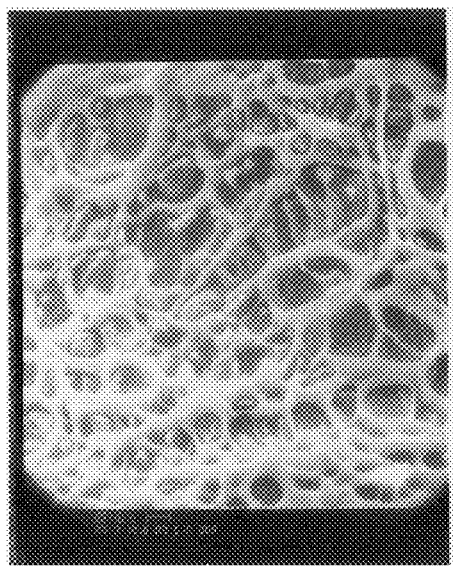 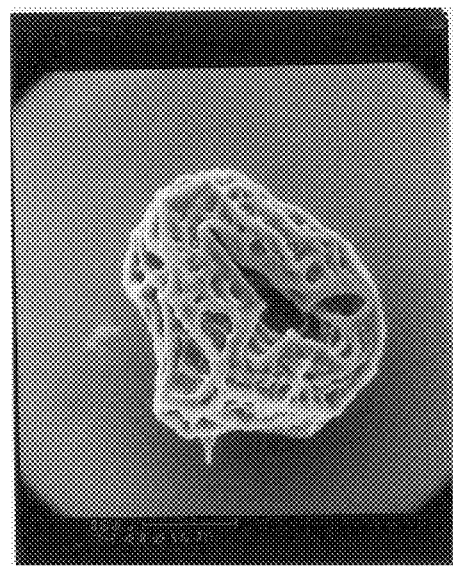
Fig. 11                    Fig. 12

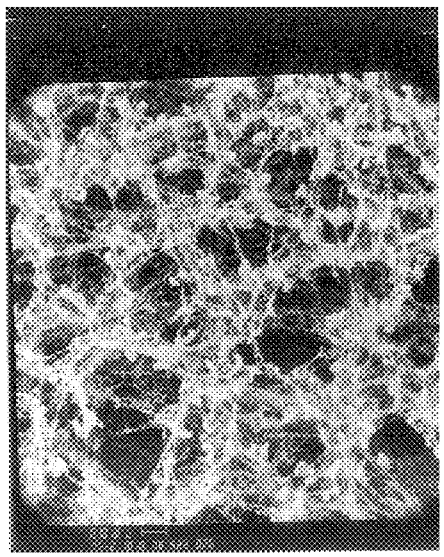 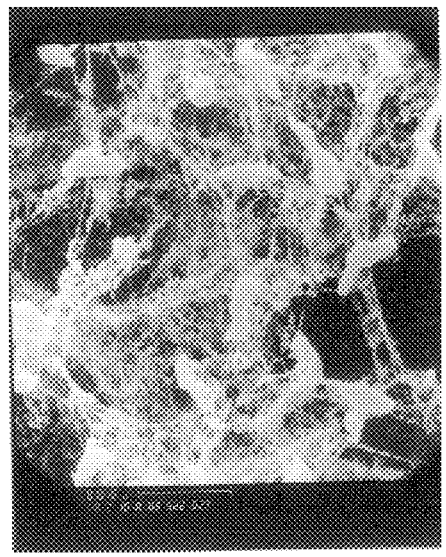
Fig. 19                    Fig. 20

REVERSIBLY SWELLABLE STARCH PRODUCTS

BACKGROUND OF THE INVENTION

1. Field of the Invention

The present invention is broadly concerned with rapidly hydratable, reversibly swellable modified starch products having unique properties, methods of preparing such starch products and thickener compositions and food products containing the starch products. More particularly, the modified starch products of the invention are in the form of individual, chemically cross-linked starch granules which are capable of undergoing multiple swelling/drying cycles with very little generation of starch solubles during such cycling. The products can be prepared by simultaneously swelling and cross-linking native starch granules in an aqueous system without complete gelatinization thereof, followed by heating the cross-linked granules in excess water. The starch products of the invention can be used to good effect in a variety of food products.

2. Description of the Prior Art

Granular cold water swelling starches are well known. These starches can be prepared by suspending wet native starch granules in rapidly moving hot air of high, followed by low, humidity (U.S. Pat. No. 4,280,851), or by heating starch in an excess of water/alcohol with subsequent removal of liquid (U.S. Pat. No. 4,465,704).

When known granular cold water swelling starches are placed in hot or cold water, the granules swell excessively and release starch solubles into the aqueous phase. Upon drying, the individual swollen starch granules collapse and fuse together. Fused dried granules can be reground, but do not thereafter thicken efficiently and give dull appearing pastes.

As a consequence of these properties, typical cold water swelling starches have only limited utility in food systems where gelling is to be avoided, e.g., in broths or other watery foods. In such systems, the conventional starches swell and gelatinize and release amylose, and upon storage give the food an unappealling mouth feel. In addition, the fact that the known starches are not reversibly swellable (i.e., they are incapable of undergoing successive swelling/drying cycles) limits the utility of the starches.

Another factor important in food grade starches relates to the in vivo digestive properties thereof.

In 1987 Englyst and Cummings at the MRC Dunn Clinical Nutrition Center in Cambridge, UK, proposed a classification of starch based on its likely digestive properties in vivo. They also devised in vitro assay methods to mimic the various digestive properties of starch. Three classes of dietary starch were proposed:

(1) Rapidly Digestible Starch (RDS). RDS is likely to be rapidly digested in the human small intestine; examples include freshly cooked rice and potato, and some instant breakfast cereals.

(2) Slowly Digestible Starch (SDS). SDS is likely to be slowly yet completely digested in the small intestine; examples include raw cereal starch and cooked pasta.

(3) Resistant Starch (RS). RS is likely to resist digestion in the small intestine. RS is thus defined as the sum of starch and starch degradation products not likely to be absorbed in the small intestine of healthy individuals. RS can be subdivided into four categories depending on the cause of resistance (Englyst et al Eur. J. Clin. Nutr. 46(suppl 2):S33, 1992; Eerlingen et al Cereal Chem. 70:339, 1993).

$RS_1$. Physically inaccessible starch due to entrapment of granules within a protein matrix or within a plant cell wall, such as in partially milled grain or legumes after cooling.

$RS_2$. Raw starch granules, such as those from potato or green banana, that resist digestion by α-amylase, possibly because those granules lack micropores through their surface.

$RS_3$. Retrograded amylose formed by heat/moisture treatment of starch or starch foods, such as occurs in cooked/cooled potato and corn flake.

$RS_4$. Chemically modified starches, such as acetylated, hydroxypropylated, or cross-linked starches that resist digestion by alpha-amylase. Those modified starches would be detected by the in vitro assay of RS. However, some $RS_4$ may not be fermented in the colon.

$RS_1$, $RS_2$, $RS_3$ are physically modified forms of starch and become accessible to α-amylase digestion upon solubilization in sodium hydroxide or dimethyl sulfoxide. $RS_4$ that is chemically substituted remains resistant to α-amylase digestion even if dissolved. $RS_4$ produced by cross-linking would resist dissolution.

$RS_3$ has been of increasing interest as a food ingredient. Unlike common dietary fiber sources, $RS_3$ does not hold much water and, thus may be a preferred fiber source for use in low moisture products such as cookies and crackers. Also, $RS_3$ is free of a gritty mouthfeel, and unlike traditional fiber sources does not significantly alter flavor and textural properties of foods. Those characteristics can improve the processing and quality of foods such as baked and extruded products when RS is added. Furthermore, $RS_3$ constitutes dietary fiber, and may be assigned much reduced calories.

SUMMARY OF THE INVENTION

The present invention provides novel modified starch products, methods of preparation thereof and thickeners and food products incorporating the starch products. Broadly speaking, the modified starch products of the invention comprise individual, chemically cross-linked starch granules having a number of novel properties. For example, the products of the invention are reversibly swellable, i.e., they are capable of undergoing multiple cycles in swelling 95° C. water for a period of 30 min. followed by drying at 105° C. to a moisture content of less than about 10% by weight (wet basis) while substantially retaining the individuality of the starch granules (as observed by microscopy). Similarly, the preferred starches can undergo multiple cycles of swelling in 25° C. water for a period of 10 min. followed by drying at 105° C. to a moisture content of less than about 10% by weight wet basis while still retaining the individuality of the starch granules. The starches hereof can also undergo multiple swelling/drying cycles with no more than about 2% by weight starch solubles, based upon the weight of the starting starch product, present in the swelling water during each of the multiple swellings; more preferably, the starches should exhibit no more than about 2% by weight starch solubles in the water during the first of the cycles, and no more than about 1% by weight starch solubles in the water during each of the succeeding cycles. Additionally, during such swelling/drying cycles, the granules exhibit a swelling power which is at least about 100% greater (more preferably at least about 200% greater) than the swelling power of the starch granules in the dried condition thereof. Preferred starches of the invention should also be capable of absorbing their own weight in water during the multiple swelling/drying cycles, more preferably at least about 200% of their own weight in water absorption. In terms of α-amylase digestion, the starches hereof should have at least about 3% resistance using AOAC Method 992.16(1995), and more preferably at least about 10% resistance.

The modified starches of the invention can be prepared using a wide variety of native starches, such as those selected from the group consisting of cereal, root, tuber, legume and high amylose starches. Particularly preferred starches are those of wheat, corn, waxy corn, high amylose corn, oat, rice, tapioca, mung bean and potato. Substituted starches can also be used as starting materials in the invention, e.g., starches having hydroxypropyl or hydroxyethyl ethers as substituents. The starches are cross-linked using cross-linkers selected from the group consisting of phosphorylating agents and epichlorohydrin. Particularly preferred cross-linkers are those selected from the group consisting of sodium trimetaphosphate, sodium tripolyphosphate and mixtures thereof. Where a phosphorylating agent is used, the final starch granules generally have at least about 0.1% by weight residual phosphorus therein.

The starches of the invention are made by a process involving first forming a dispersion of starch granules in water where the granules undergo swelling in the dispersion and have a crystalline phase. A cross-linking agent is added to the dispersion while the granules are swelled in order to cross-link the swelled granules, the cross-linking being carried out under conditions to avoid complete gelatinization of the swelled granules. Thereafter, the cross-linked starch granules are heated in excess water in order to melt the crystalline phase of the granules.

In a preferred procedure, the starch granules are preswelled by first forming a starch/water dispersion and heating the latter in order to swell the granules prior to the addition of the cross-linking agent; the preswelling step is preferably carried out in the presence of a base (such as an alkali metal hydroxide which promotes swelling) and a salt (such as an alkali or alkaline earth metal chloride, sulfate or carbonate). Again, it is important that the preswelling and cross-linking steps be carried out so as to avoid complete gelatinization of the starch granules. Accordingly, the temperature of the starch dispersion during preswelling is generally 5–10° C. below the starch gelatinization temperature. It is also possible to preswell the starch at elevated temperatures, for example 70–80° C. if high concentrations (greater than about 20% based on starch) of salt are used with reduced amounts of base. The hydroxide is normally present at a level of about 1–3% by weight based upon starch, while the salt is used at a level of from about 5–25% by weight on the same basis. The pH of the preswelling system is generally from about 10–12.

During the cross-linking step (whether or not a preswelling step has been carried out), the dispersion should have from about 20–40% by weight of starch solids therein. The cross-linking step generally involves heating to a temperature of from about 30–75° C. for a period of from about 0.1–3 hrs., more preferably from about 0.5–1 hr. Where the preferred combination of sodium trimetaphosphate (STMP) and sodium tripolyphosphate (STPP) are used as the phosphorylating agent, the mixture is generally used at a level of from about 2–12% on a dry starch basis. The weight ratio of STMP to STPP is preferably about 99:1. The higher the level of STMP/STPP used, the faster the cross-linking reaction and the higher the level of α-amylase digestion resistance, but the lower the swelling power of the final product. During cross-linking, if too low a level of STMP/STPP is added, the starch will eventually gelatinize and cause the reaction mixture to gel. When this occurs, swelling has not been counterbalanced by sufficient inhibition from cross-linking. Increasing the temperature of the cross-linking reaction is a compromise between accelerating the swelling and accelerating the cross-linking reaction, such that gelling of the reaction mixture does not occur prior to sufficient cross-linking in a reasonable period of reaction time. After reacting at a warm temperature usually for several hours, the mixture is neutralized and the starch isolated from the salts to give quantitative product yields. The product exhibits an X-ray diffraction pattern very similar to the starting starch, and a gelatinization temperature somewhat elevated as compared with the parent starch. Most often the products exhibit 5–70% $RS_4$, and when using hydroxypropylated starches as starting materials, $RS_4$ levels reach 70% and higher.

In the final preferred preparative step, the partially crystalline, swollen/cross-linked starches are heated in excess water followed by drying in order to melt the crystalline phase. For example, a 10% aqueous slurry of the partially crystalline product may be heated to boiling with stirring for about 5 min. to achieve this end. The boiled product is then cooled and centrifuged. The liquid fraction contains at most 1–2% of the original weight of the partially crystalline modified starch in the form of soluble and damaged starch. If the starches are merely tray dried without removal of the soluble and damaged starch fraction, the product may form a cake-like structure comprised of granules that cling together. In lieu of centrifugation, the starch products may be spray dried.

The starches of the invention dry very rapidly and will rehydrate almost instantly in water. The starches are amorphous as determined by X-ray diffraction and upon rehydration the products swell to the same bulk volume.

As indicated, the products of the invention can undergo cycles of hot or cold temperature swelling in water and drying many times (at least five) without losing the individuality of the starch granules. After drying, the products immediately redisperse in cold or hot water and give fully swollen opaque-appearing granules with practically no lost solubles in the aqueous phase; this is true even when the granules are boiled repeatedly in water for over 2 hrs. Such swelling/drying cycles do not appreciably reduce the swelling power of the starches, leading to the conclusion that rehydration of the granules involves water filling the void spaces formed in the granules, rather than conventional hydration of the starch granules.

The products of the invention can be used in a wide variety of contexts. For example, they may be used with gums to form food thickeners. Thickeners would typically include the starch products at a level of from about 5–15% by weight, with the gum being present at a level of from about 0.03–1% by weight. Suitable gums are those selected from the group consisting of guar, xanthan, karaya, acacia and tragacanth gums.

The starch products can be used in a wide number of food products including all types of leavened and unleavened baked or fried cereal grain-containing foods, e.g., breads, rolls, pastries, and cookies, and in other products such as salad dressings. In such uses, the starches could be used as a fat-replacer where the swollen granules are perceived as a smooth, mobile solid, resembling the texture of fat. In addition to food products, the hydration and other properties of the starches make them suitable for incorporation into cosmetic and personal care products (e.g., shampoos, makeup, lotions and creams for skin care, and talc substitutes), into pharmaceutical dosage forms such as medicament-containing tablets, and/or desiccants.

BRIEF DESCRIPTION OF THE DRAWINGS

FIG. 3 is a 2000×magnification SEM of the wheat starch of FIG. 2;

FIG. 4 is a 5000×magnification SEM of the wheat starch of FIG. 2;

FIG. 11 is a 5000×magnification SEM of the starch of FIG. 9;

FIG. 12 is a 2000×magnification SEM of granular, reversible cold-water swelling wheat starch after autoclaving swollen/cross-linked wheat starch (0.28% phosphorus) in 10 parts water at 125° C. for 10 min, and a sample was isolated and prepared for SEM;

FIG. 19 is a 500×magnification SEM of cooked tapioca starch after prime tapioca starch was heated in 20 parts water to 100° C. to form a paste, the paste was centrifuged, the sediment washed with cold water and dried at 100° C., and a sample was isolated and prepared for SEM;

FIG. 20 is a 2000×magnification of the starch of FIG. 19;

DETAILED DESCRIPTION OF THE PREFERRED EMBODIMENT

Figure 1:
FIG. 1 is a scanning electron micrograph (SEM) of prime wheat starch prepared for SEM by addition of prime wheat starch to excess water at 25° C., placing an aliquot on a SEM stub, drying under vacuum, and coating the sample and viewing at 2000×magnification.

The following examples set forth preferred modified starch products in accordance with the invention, as well as methods of preparing such products. It is to be understood however, that these examples are provided by way of illustration only, and nothing therein should be taken a limitation upon the overall scope of the invention.

EXAMPLES

Materials and Methods

The following describes the materials and general methods used in the Examples; all literature references, including test methods, are incorporated by reference herein.

Materials

The following items were purchased from Sigma Chemical Co (St. Louis, Mo.); corn and potato starches, sodium trimetaphosphate (STMP), sodium tripolyphosphate (STPP), 2-(N-morpholino)ethanesulfonic acid (MES, Cat. No. M 8250), tris(hydroxymethyl)aminomethane (TRIS, Cat. No. T 1503), and total dietary fiber assay kit (TDF-100 A). The dietary fiber kit included heat stable α-amylase, with 47,000 U/ml, where 1 unit will liberate 1.0 mg of maltose from starch in 3 min at pH 6.9 and 20° C., amyloglucosidase, with 3690 U/ml, where 1 unit will liberate 1.0 mg of glucose from starch in 3 min at pH 4.5 and 20° C., and protease with 7–15 U/g, where 1 unit will produce a $A_{280}$ of 0.5 in 30 min at pH 7.5 and 30° C. measured as TCA soluble products using N,N-dimethylated casein as substrate. Glucose assay kit (Cat No 716251) was purchased from Boehringer Mannheim (Indianapolis, Ind). Wheat starch (Midsol 50) and hydroxypropylated (~4.5%) wheat starch (Midsol 40) were from Midwest Grain Products Co. (Atchison, Kans.); tapioca starch, waxy corn starch (Amioca), high amylose corn starch (Hylon V), drum-cooked modified waxy maize (National 5717), pregelatinized modified tapioca (National 104), cold-water swelling modified waxy corn starch (Ultra-Tex 4), cold-water swelling modified tapioca starch (Ultra-Tex 3), and cold-water swelling modified waxy maize starches (Ultra-Sperse 5, Ultra-Sperse), were from National Starch and Chemical Company (Bridgewater, N.J.). Granular cold-water swelling modified waxy maize starches (Mira-Thik 603 and Mira-Sperse 623), pregelatinized modified tapioca (Binasol 15), and modified waxy maize (Sta-O-Paque), were from A. E. Staley Manufacturing Company (Decatur, Ill.). Potato starch was from Penford Food Ingredients, Englewood, Colo. Phosphoryl chloride and epichlorohydrin were from Aldrich Chemical Company (Milwaukee, Wis.). Cookie flour was a soft wheat flour with 12.0% moisture, 0.51% ash, and 9.6% protein, all on a wet basis.

General Methods

All chemical analyses were done in triplicate. Ash (Method 08 - 01) and moisture (Method 44 - 15) contents were determined by American Association of Cereal Chemists Official Methods (1995), and the phosphorus levels in starch (5–10 g sample size) were determined by the procedure of Smith and Caruso, *Methods of Carbohydrate Chemistry* 4:42(1964). Unless otherwise stated, the phosphorus levels include naturally occurring phosphate in starch plus that reacted with starch. Total carbohydrate was done by the phenol-sulfuric acid method of Dubois et al, *Analytical Chemistry* 28:350 (1956), incorporated by reference herein. X-ray diffraction of starch was done on samples stored at 23 ° C. and 95% relative humidity for 24 h. X-ray diffractograms were obtained with a Philips (Model 42273) x-ray diffractometer (Philips, Mahwah, N.J.) operated at 35 KV and 20 mA. X-ray diffraction patterns of starch were taken with Cu/Ni foil filtered, $K_a$ radiation. The samples were scanned through 2 θ (diffraction angle) range of 5–35° at 2° ×2 θ per min. A step interval of 0.01° θ and a count time of 1 sec were used.

Scanning electron micrographs (SEM) were taken with a Perkin-Elmer Etec-Autoscan U-1 microscope at an accelerating potential of 20 kv. The starch samples were added onto double-sided adhesive tape on top of specimen stubs, vacuum dried and then coated with gold.

Solubility and swelling power ($SP_{95}$) of starches were determined by a modification of the method of Leach et al., *Cereal Chemistry* 36:535 (1959), incorporated by reference herein. Starch (0.5 g) and water (30 mL) were placed in a polypropylene centrifuge tube, and the tube was capped and heated in a boiling water bath. While heating, the tube was inverted several times the first minute of heating and then once every 5 min. After 30 min, the hot paste was centrifuged, and an aliquot removed for immediate assay of total carbohydrate. The concentration of soluble carbohydrate multiplied by the volume of supernatant gave the percent solubles. The remainder of the supernatant was removed with care, which involved use of a hypodermic syringe and needle in the case of sedimented starch with low cohesion. The weight of the gel phase divided by its dry solids (total starch minus soluble starch) equaled the swelling power at 95° C. in g/g.

Solubility and swelling power of pregelatinized and cold-water swelling starches were done also in water at 25 ° C. using the same procedure.

Pasting behavior of starch was measured in a Rapid ViscoAnalyzer (Foss N. America, Eden Prairie, Minn.). Starch (3.0 g) and water (25 mL) containing 175 mg of dissolved guar gum (0.7%), were added to a sample cup, and the mixture was equilibrated to 50° C. for 4 min in the instrument, followed by heating to 95° C. for 8 min, holding at 95° C. for 2 min, then cooling to 50° C. in 8 min. The starting paste consistency in Rapid ViscoAnalyzer Units (RVU), gelatinization temperature in ° C., peak consistency at 95° C., and the consistency upon cooling were determined from RVA curves.

Determination of RS by the Total Dietary Fiber Method

RS was determined using the Sigma kit TDF-100A for Method 991.43 of the American Association of Official Analytical Chemists (1995), incorporated by reference herein. That method measures total dietary fiber in foods. Starch (1 g) was dispersed in 0.05 M MES-TRIS buffer solution (40 mL, pH 8.2) in a 400 ml tall-form beaker, and heat-stable α-amylase solution (50 μL, 700 U) was added. The beaker was covered with aluminum foil and placed in a waterbath at 95–100° C. for 35 min, during which time the contents were gently stirred with a magnetic stir bar or swirled every 5 min by hand. The stirred or swirled digestions gave the same results, but swirling was more convenient for large numbers of samples. After cooling to 60° C., protease (100 μl) was added and the mixture incubated for 30 min and continuously stirred at low speed. The solution was adjusted to pH 4.0–4.7 by adding 0.56 M HCl (4.0–4.5 ml) solution, and amyloglucosidase solution (300 μl) was added. After incubating for 30 min, 4 volumes of 95% ethanol (~200 ml, preheated to 60° C.) was added, and the mixture allowed to stand for 1 h at room temperature. The precipitate was collected on a tared sintered glass crucible (Porosity No. 2) over a dried bed of diatomaceous earth (1.0 g) as filter aid. The insoluble residue was washed with distilled water (2×15 ml), 78% ethanol, absolute ethanol, and acetone. The crucibles with the residue were dried overnight in a forced draft oven at 105° C., and weighed after cooling to room temperature in a desiccator over anhydrous calcium sulfate. RS was the insoluble residue expressed as the percentage of starch on a dry basis.

Example 1

Wheat Starch Cross-Linked After Preswelling in Aqueous Sodium Hydroxide/Sulfate Wheat starch (20 g, dry basis), water (80 ml), and sodium sulfate (5 g, 10%, starch basis, sb) were placed in a 400 ml tall-form beaker, and the mixture was adjusted to pH ~11.5 by adding 1.0 M sodium hydroxide (15 mL). The slurry was stirred continuously, warmed, and held at 45° C. for 1h. After that time 2.4g (12%, sb) of a 99/1 (w/w) mixture of STMP/STPP was added to the slurry, and the reaction mixture stirred an additional 3h at 45 ° C. The slurry was then adjusted to pH 6.5 by adding 1 M hydrochloric acid (12–14 ml), and the starch was collected by centrifugation, washed with water (4×100 ml) and dried at 40° C. The yield of swollen/cross-linked starch was quantitative. The product gave an A-type x-ray diffraction pattern with strong reflections at 2θ of 15.5°, 17.9° and 23.4°, and its scanning electron micrograph (FIG. 5) showed a granular product with somewhat swollen appearance compared to unmodified wheat starch (FIG. 1). The starch gelatinized in excess water at $T_0$ 65 ° C., $T_p$ 67° C. and $T_c$ 71° C. with an enthalpy of gelatinization equal to 6.6 J/g as determined by differential scanning calorimetry. The starch showed 0.28% phosphorus, no sulfate, and gave less than 0.1% solubility and swelling power ($SP_{95}$) of 6.4 g/g upon heating to 95° C. in 60 parts of water. It contained 31% (db) of resistance starch, and 0.8% lipid that was extractable with hot propanol/water, 3/1, v/v. Its pasting curve with 12% starch solids in 0.7% guar gum showed a gelatinization temperature of~70° C., peak consistency 25, and final consistency at 50° C. of 42 RVU.

Granular Reversible Cold-Water Swelling Starch

The swollen/cross-linked, partially crystalline starch (5 g) was dispersed in water (100 mL) in an erlenmeyer flask, and the flask was placed in a boiling water bath and heated to 95° C. while continuously stirring the contents for 30 min. The swollen starch was isolated by centrifugation (1000×g, for 20 min), washed with water (2×100 ml) and dried at 105° C. The product which contained ~80% moisture was bone-dry in 2 h at 105° C., while a wheat starch paste with 93% moisture reached 78% moisture under identical drying conditions. The soluble starch in the supernatant plus washings of the modified wheat starch was determined to be less than 0.1% by the phenol-sulfuric acid method. The dried product, after preparation for scanning electron microscopy was granular (FIGS. 6–8), and it contained 0.28% phosphorus, the same as the uncooked starch, and 9% resistant starch. Its pasting curve at 12% starch solids in 0.7% guar solution gave an initial paste consistency of 60 RVU at 50° C., 40 RVU at 95° C., and 55 RVU again at 50° C., and its iodine binding capacity (9% by weight) was approximately one-half that of granular prime wheat starch (16% by weight). The dried product was heated in water (5 ml) to 95° C. with stirring, and after 30 min the mixture was centrifuged (1,000×g). The supernatant was assayed for total carbohydrate, and the sedimented starch was dried to constant weight at 100 ° C. The heating and drying steps were repeated 4 more times, and solubility and swelling power of the instant starch were determined.

TABLE 1

Reversibility of Swelling of the Modified Wheat Starch (P = 0.28, $SP_{95}6.4$) Upon Repeated Heating in Water and Drying at 95–100° C.

| Cycle No. | Solubility, % | Swelling Power, g/g | Resistant Starch, % |
|---|---|---|---|
| 1 | below 0.1% | 5.8[a] | 9 |
| 5 | below 0.1% | 5.8[a] | 6 |

[a]Product had the same swelling power at 25° C..

The data in Table 1 shows practically no change in hot-water solubility or swelling power after repeated wetting and drying at high temperature, and FIGS. 9–12 show the product remained granular. The level of resistant starch ($RS_4$), however, decreased from 9% initially to 6% after five wetting/drying cycles.

Example 2
A Family of Granular Reversible Cold-Water Swelling Wheat Starches

A series of swelling/cross-linking reactions were done on wheat starch as set forth in Example 1, except the level of the mixture of cross-linking reagents (STMP/STPP, 99/1) was varied at 0.8, 1.6 and 2.4 g (4, 8 and 12%, sb). All the products, referred to as swollen/cross-linked starches, were obtained in quantitative yield. Their levels of phosphorus and resistant starch, as well as their swelling powers and solubilities at 95 ° C. in excess water are given in Table 2, and compares these with commercial food grade starches.

Samples of the three swollen/cross-linked wheat starches were stirred in 10 parts of water, and each mixture heated in a boiling water bath to ~95° C. for 30 min. The gelatinized starches were isolated in dry form as before in >99% yield. The maximum solubility of the starches in the aqueous cooking phase was less than 1%, so their phosphorus levels were presumed to equal those in their uncooked forms in Table 2. The products were all granular reversible cold-water swelling starches. Table 2 shows that the dried instant forms of the product starches rehydrated to the same swelling powers in cold water at 25° C. as did the swollen/cross-linked starches when heated for 30 min in excess water at 95° C. Moreover, the instant starches gave the same swelling power in water at 95° C. as in water at 25° C.

Granular Reversible Cold-Water Swelling Starches Prepared from Various Starches

Swollen/cross-linked starches and their instant forms were prepared according to Example 1 from normal corn, waxy corn, high-amylose corn, tapioca, potato and hydroxypropylated (~4.5%) wheat starches. The swollen/cross-linked products contained 0.08–0.38% of phosphorus, and gave less than 1% solubility in hot water at 95 ° C. with swelling powers of 3.8 to 9.7 g/g (Table 2). Upon heating in water, washing and drying at 100° C., they all gave granular reversible cold-water swelling forms as evidenced by FIGS. 6–8, 16–18, and 21–22 and by their solubilities and swelling powers which predominantly did not change after one cycle of wetting in excess water and drying, both at 100° C. (Table 2). The swollen/cross-linked products contained from 2–70% resistant starch ($RS_4$), and their instant forms were presumed to contain $RS_4$ because their phosphorus levels remained unchanged.

In order to contrast swelling and drying properties of the new starches, ten commercial starches were selected for comparison based on their resistance to shear and acid, and on their being pregelatinized (National 5717, National 104 and Binasol 15) or being granular cold-water swelling (Ultra-Tex 3, Ultra-Tex 4, Ultra-Sperse 5, Ultra-Sperse M, Mira-Thick 603 and Mira-Sperse 623). Table 2 shows that all the chosen commercial starches had high solubilities of 10–47% and high swelling powers of 12–26 g/g. Two of the commercial granular cold-water swelling starches were heated in excess water, their pastes centrifuged, and their supernatants discarded. Each sediment was washed with water several times, the washings discarded, and the sediment dried at 100° C. Both dried products were tough when ground, and microscopy showed the materials were not comprised of individual granules, indicating irreversible swelling properties. The ground dried ground materials, which are named instant forms in Table 2, gave reduced swelling powers at 25 ° C.

TABLE 2

Swollen/Cross-Linked Starches and Their Instant Forms, and Commercial Starches

| | | Swollen/Cross-Linked Starches | | | | Instant Form |
|---|---|---|---|---|---|---|
| Starch | Level of 99/1 (w/w) STMP/STPP, % | % Phosphorus | % Resistant Starch | % Solubility at 95° C. | Swelling Power g/g 95° C. | Swelling Power, g/g 25° C. |
| New Starches | | | | | | |
| Wheat (blank) | — | 0.06 | 0 | 18 | 14.7 | 2.7 |
| Wheat | 12[a] | 0.38 | 70 | <1 | 6.8 | 6.8 |
| Wheat | 12 | 0.28 | 31 | <1 | 6.4 | 6.4 |
| Wheat | 8 | 0.18 | 7 | <1 | 6.9 | 6.8 |
| Wheat | 4 | 0.09 | 2 | <1 | 7.3 | 7.6 |
| Hydroxypropyl wheat (blank) | — | <0.01 | <1 | 13.6 | 22.9 | 12.8 |
| Hydroxypropyl wheat | 12 | 0.14 | 6.2 | 1.9 | 9.7 | 11.1 |
| Corn (blank) | 0 | 0.02 | 0 | 7.3 | 16.7 | 3.6 |
| Corn | 12 | 0.14 | 12 | <1 | 5.9 | 5.9 |

TABLE 2-continued

Swollen/Cross-Linked Starches and Their Instant Forms, and Commercial Starches

| Waxy corn (blank) | — | <0.01 | 0 | 14.2 | 35.4 | 4.5 |
| Waxy corn | 12 | 0.20 | 8 | <1 | 8.3 | 8.3 |
| Amylomaize (blank) | — | 0.02 | 26 | 5.3 | 8.7 | 1.7 |
| Amylomaize | 12 | 0.13 | 63 | 1.1 | 3.8 | 4.5 |
| Potato (blank) | — | 0.07 | <1 | ~100 | v. high | 5.1 |
| Potato | 12 | 0.25 | 42 | <1 | 6.7 | 6.7 |
| Tapioca (blank) | — | <0.01 | <1 | 100 | v. high | 16.1 |
| Tapioca | 12 | 0.08 | 10 | <1.0 | 6.3 | 4.7 |
| Mung bean (blank) | — | 0.02 | <1 | 8.8 | 13.2 | 4.6 |
| Mung bean | 12 | 0.17 | 48 | <1.0 | 5.1 | 5.1 |

Commercial Starches

| Starch | Pregelatinized or Instant-Granular Starches | | | | Hydrated and Dried Form |
|---|---|---|---|---|---|
| | % Phosphorus | % Resistant Starch | % Solubility at 95° C. | Swelling Power, g/g 95° C. | Swelling Power, g/g 25° C. |
| National 5717 | <0.01 | <1 | 17 | 17.0 | — |
| National 104 | <0.01 | <1 | 9.5 | 8.5 | 12.7 |
| Ultra-Tex 3 | <0.01 | <1 | 47 | 25.8 | 16.4 |
| Ultra-Tex 4 | <0.01 | <1 | 22 | 20.4 | — |
| Ultra-Sperse 5 | <0.01 | <1 | 21 | 20.5 | — |
| Ultra-Sperse M | <0.01 | <1 | 17 | 20.1 | 14.8 |
| Mira-Thick 603 | 0.05 | <1 | 20 | 19.1 | — |
| Mira-Sperse 623 | 0.06 | <1 | 22 | 20.1 | 16.0 |
| Binasol 15 | <0.01 | <1 | 28 | 11.9 | — |
| Sta-O-Paque | <0.01 | 4 | 17 | 23.2 | 18.6 |

[a]Cross-linked 5 h with 12% STMP/STPP (99/1, w/w) at pH 11.5 with 10% sodium sulfate; other cross-linking reactions done in the same manner except 3 h.

Example 3
Scanning Electron Microscopy (SEM)

Swollen/cross-linked starches were prepared from cereal, tuber, and root starches, and the products were cooked and dried to give reversible, cold-water swelling starches. The various swollen/cross-linked starches, their phosphorus levels, and swelling powers at 95° C. were as follows: wheat, 0.28%, 6.4 g/g; potato, 0.25%, 6.7 g/g; and tapioca 0.08%, 6.3 g/g. Each starch was cooked in excess water according to Example 1 and dried at 100° C. In addition, the swollen/highly crossed-linked wheat starch was subjected to 5 cycles of cooking and drying at 100° C. The three parent starches were cooked and dried for comparison. Immediately after cooking a parent starch, the hot 5% paste was centrifuged, the supernatant discarded, and the sediment washed with cold water with shaking by hand. After the final centrifugation, the swollen granules in the sediment were dried at 100° C.

Dried starch (~100 mg) was dispersed in water (1 mL) at 25° C., and an aliquot (0.05 mL) was placed atop a sample-holder stub for scanning electron microscopy. After drying under vacuum, the sample was viewed by SEM.

Figure 2:
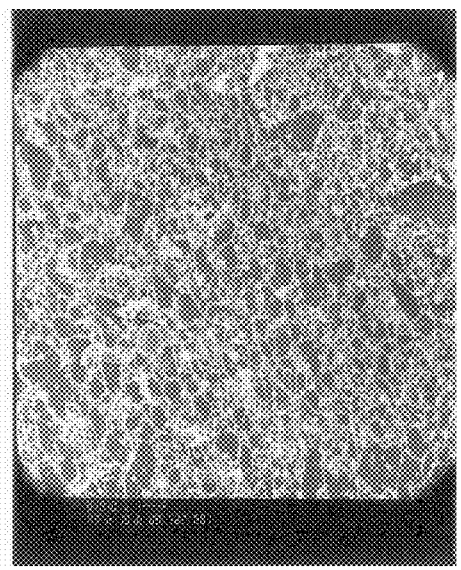
FIG. 2 is a 500×magnification SEM of cooked wheat starch after prime wheat starch was heated in 20 parts water to 100° C. to form a paste. The paste was centrifuged, the sediment washed with cold water, and the washed sediment dried at 100° C.; the dried sample was resuspended in water and prepared for SEM.
Figure 5:
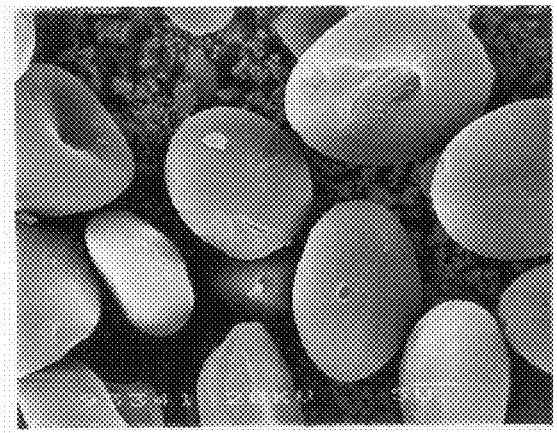
FIG. 5 is a 2000×magnification SEM of swollen/cross-linked wheat starch in accordance with the invention.

FIG. 1 shows prime wheat starch, and FIGS. 2–4 show the same starch after cooking. The cooked wheat starch shows filamentous strands clinging to small, swollen wheat starch granules. The large granules in the uncooked prime starch (FIG. 1) are disk-shaped and have a smooth surface, whereas the large granules in cooked wheat starch (not shown in FIGS. 3–4) show a distorted shape with filaments of soluble polymer molecules on their surface. Upon drying, the swollen large granules and filaments cohere. The distortion of the large wheat starch granules after cooking and drying cause them to appear as saddles or rosettes, and those shapes have been previously reported for Triticeae starches by Williams and Bowler, Starch/Staerke 34:221 (1982). The filamentous material is a collection of mostly amylose molecules as first observed in SEM by Miller et al., Cereal Chem, 50:271 (1971). FIG. 5 shows swollen/cross-linked wheat starch. This cross-linked starch appears to have a similar but swollen shape compared to the prime wheat starch depicted in FIG. 1.

Figure 6:
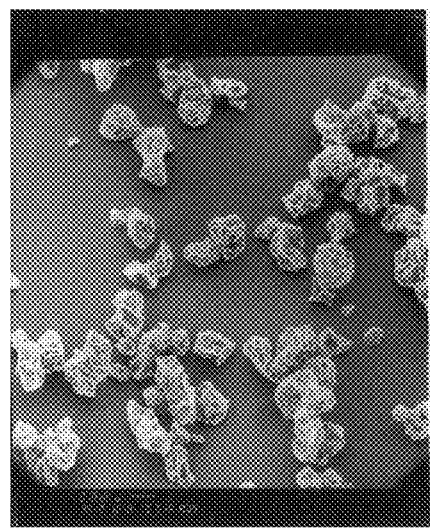
FIG. 6 is a 500×magnification SEM of granular, reversible cold-water swelling wheat starch wherein swollen/cross-linked wheat starch of the type shown in FIG. 5 with 0.28% phosphorus and swelling power at 95° C. of 6.4 g/g, was heated in 20 parts water to 100° C., whereupon the hot mixture was centrifuged, the sediment washed with cold water and dried at 100° C., and a sample was isolated and prepared for SEM.
Figure 7:
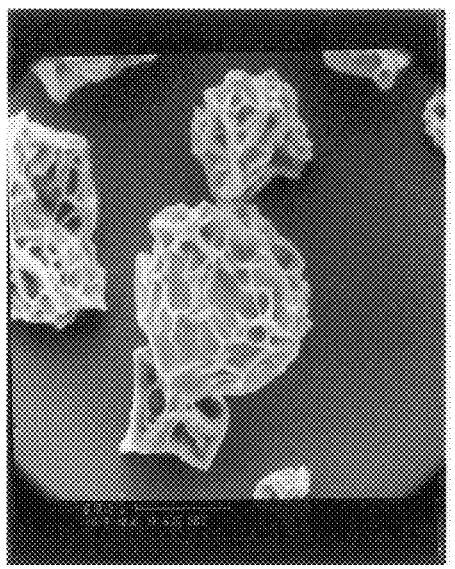
FIG. 7 is a 2000×magnification SEM of the starch of FIG. 6.
Figure 8:
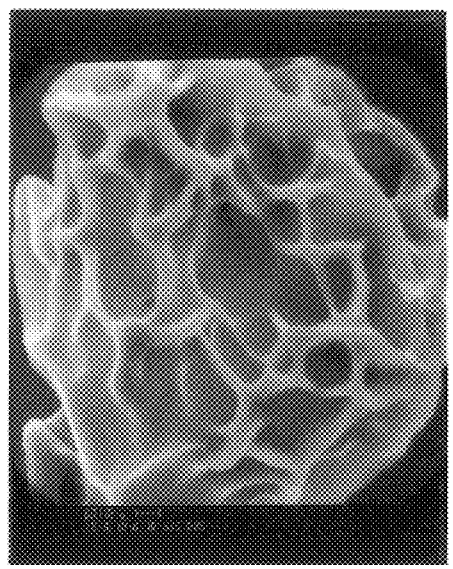
FIG. 8 is a 5000×magnification SEM of the starch of FIG. 6.
Figure 9:
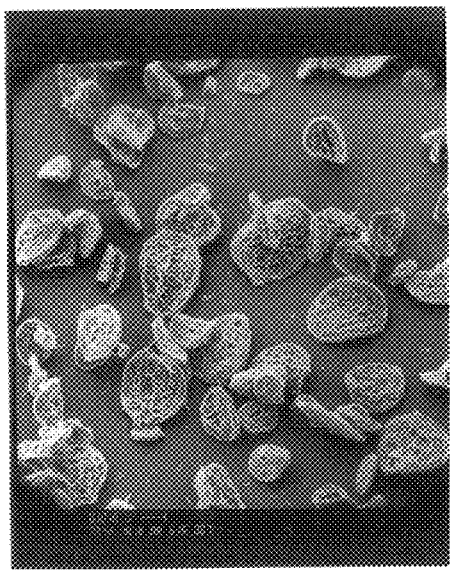
FIG. 9 is a 500×magnification SEM of granular, reversible cold-water swelling wheat starch after five cycles of cooking and drying, both at 100° C., and a sample was isolated and prepared for SEM.
Figure 10:
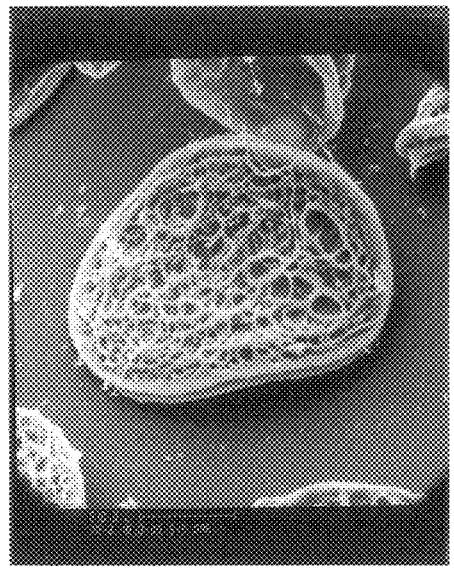
FIG. 10 is a 2000×magnification SEM of the starch of FIG. 9.
Figure 13:
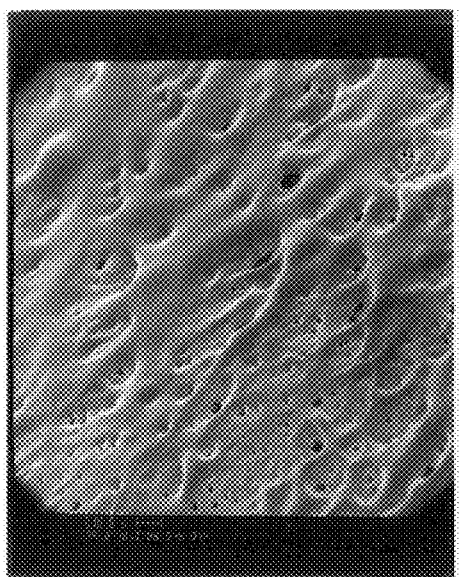
FIG. 13 is a 500×magnification SEM of cooked potato starch after prime potato starch was heated in 20 parts water to 100° C. to form a paste, the paste was centrifuged, the sediment washed with cold water and dried at 100° C., and a sample was isolated and prepared for SEM.
Figure 14:
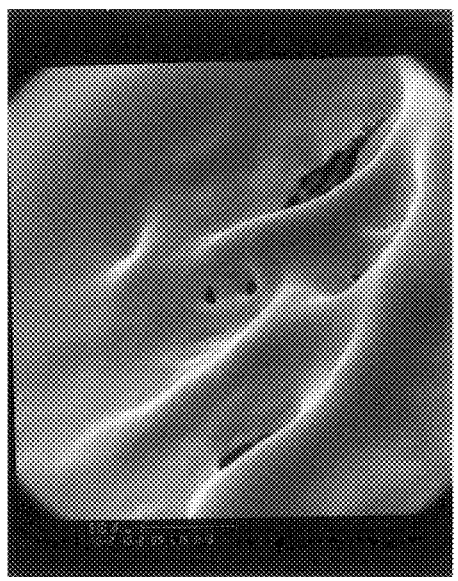
FIG. 14 is a 2000×magnification SEM of the starch of FIG. 13.
Figure 15:
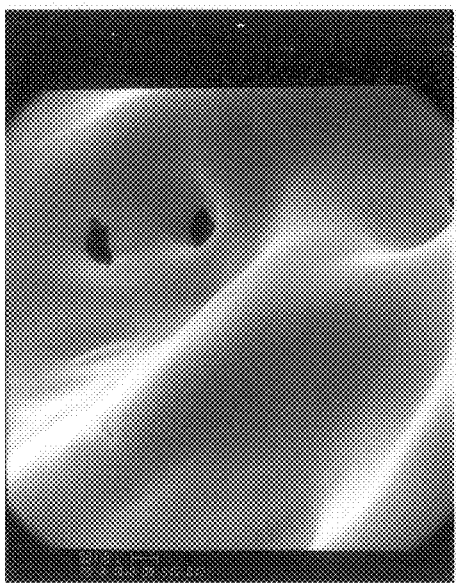
FIG. 15 is a 5000×magnification SEM of the starch of FIG. 13.
Figure 16:
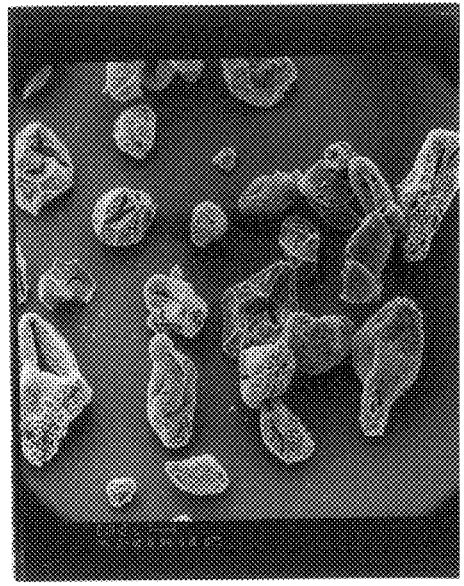
FIG. 16 is a 500×magnification SEM of granular, reversible cold-water swelling potato starch wherein swollen/cross-linked potato starch with 0.25% phosphorus and swelling power at 95° C. of 6.7 g/g was heated in 20 parts of water at 100° C. whereupon the hot mixture was centrifuged, the sediment washed with cold water and dried at 100° C., and a sample was isolated and prepared for SEM.
Figure 17:
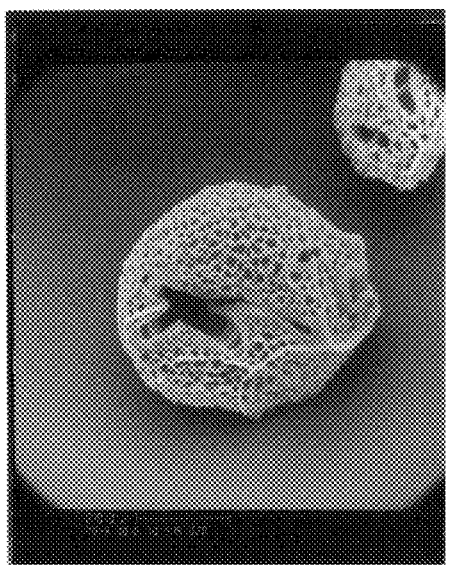
FIG. 17 is a 2000×magnification of the starch of FIG. 16.
Figure 18:
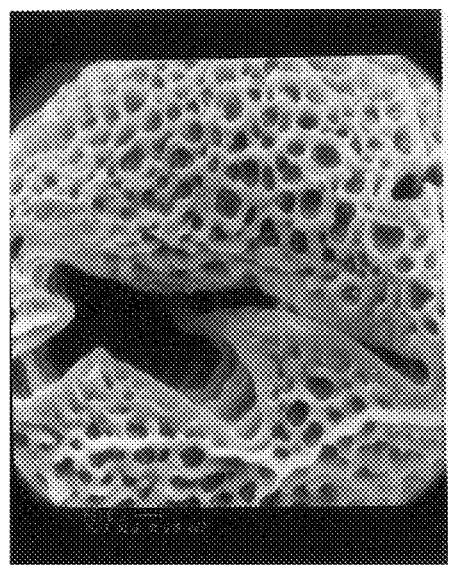
FIG. 18 is a 5000×magnification of the starch of FIG. 16.
Figure 21:
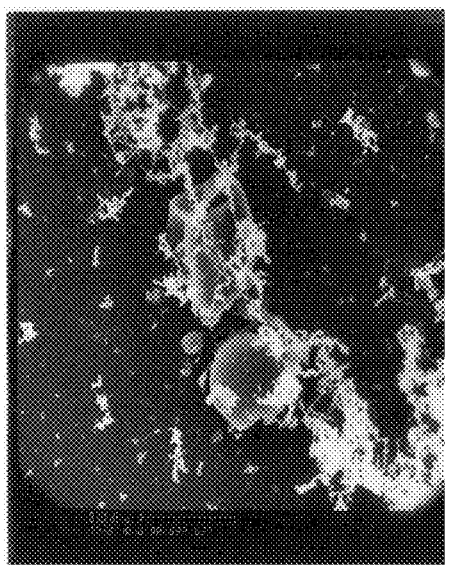
FIG. 21 is a 2000×magnification SEM of granular, reversible cold-water swelling tapioca starch wherein swollen/cross-linked tapioca starch with 0.08% phosphorus and swelling power at 95° C. of 6.3 g/g was heated in 20 parts of water at 100° C. whereupon the hot mixture was centrifuged, the sediment washed with cold water and dried at 100° C., and a sample was isolated and prepared for SEM.
Figure 22:
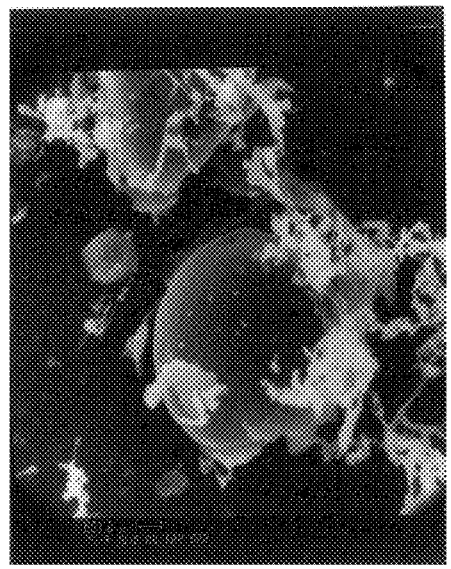
FIG. 22 is a 5000×magnification of the starch of FIG. 21.

FIGS. 6–8 show the new type starch, granular reversible cold-water swelling wheat starch; those granules show a different appearance. FIGS. 9–11 are SEMs of the same new modified wheat starch after 5 cycles of cooking/drying at 95–100° C., and FIG. 12 depicts the starch after one autoclaving (125° C.) in excess water then drying (100° C.). The granules of wheat starch of this invention swell in cold and hot water (FIGS. 6–8), but the shape of the large wheat starch granules has been retained as disks (FIG. 1), which is best observed in FIGS. 9–11. Moreover, no filamentous material was observed on or near the granules of the reversible cold-water swelling wheat starch, and the granules show little or no coherence to each other. The wrinkled surface of the granules was caused by folding of swollen starch as the material shriveled during, drying, as previously discussed for starch pastes (freeze-dried) of modified food-grade starches with low levels of cross-linking (Chabot et al., Cereal Chem, 553:85 (1976).

Cooked prime starches and their respective reversible cold-water swelling starches, are contrasted for potato in FIGS. 13–15, and 16–18, and tapioca in FIGS. 19–20, and 21–22. The cooked prime starches showed fused granules for potato starch and filamentous material for tapioca starch, whereas the new starches showed individual granules.

Example 4
Gelatinization of Starches Determined by Differential Scanning Calorimetry (DSC)

Compared to the unmodified blank starches, swollen/cross-linked starches in accordance with the invention gelatinized at approximately 2–5° C. higher in excess water (Table 3). The enthalpy of gelatinization (melting) of the crystalline phase was reduced, although one remained unchanged, due to the swelling of the granules before and during cross-linking.

TABLE 3

Gelatinization of Swollen/Cross-Linked Starches In Excess Water Determined by DSC

| Sample[a] | Temperature (° C.) | | | Enthalpy |
|---|---|---|---|---|
| | $T_O$ | $T_p$ | $T_C$ | $\Delta H(J/g)$ |
| Wheat (blank) | 56.6 | 61.4 | 66.9 | 9.8 |
| x-wheat 4 | 62.3 | 65.9 | 70.1 | 7.1 |
| x-wheat 8 | 63.7 | 66.9 | 70.9 | 6.5 |
| x-wheat 12 | 63.5 | 66.9 | 71.0 | 6.5 |
| Hydroxypropyl wheat (blank) | 50.6 | 55.5 | 60.3 | 6.3 |
| x-hydroxypropyl 12 | 53.1 | 57.5 | 62.3 | 5.0 |
| Potato (blank) | 62.0 | 66.4 | 71.8 | 13.6 |
| x-potato 12 | 64.3 | 68.2 | 72.5 | 14.5 |
| Corn (blank) | 64.3 | 69.4 | 73.7 | 11.9 |
| x-corn 12 | 67.1 | 57.5 | 62.3 | 5.07 |
| Waxy corn (blank) | 65.2 | 71.4 | 77.1 | 15.7 |
| x-waxy 12 | 67.7 | 73.1 | 77.5 | 14.5 |
| Amylomaize (blank) | 68.9 | 76.9 | 103.1 | 14.2 |
| x-amylomaize 12 | 70.5 | 78.4 | 94.7 | 10.7 |

[a]Modified starches indicated by "x", and the % level of cross-linking agent (STMP/STPP, 99/1, w/w) used at 45° C. for 3 h is listed after the name of the starch.

Example 5
Wheat Starch Cross-Linked After Preswelling in Warm Water Containing Sodium Sulfate Followed by Generation of Granular Reversible Cold-Water Swelling Starches Wheat starch (20 g, db), water (150 mL) and sodium sulfate (3 g, 15% sb) were added to a beaker, and the mixture stirred at 25° C. After 5 min, the mixture was warmed to 70° C. and held at that temperature for 30 min. Aqueous 1M sodium hydroxide (~10 mL) followed by STMP/STPP (99/1, 1.2 g, 6% sb) was added. After reacting the mixture at pH 11.5 for 30 min at 70° C., it was adjusted to pH 7 by adding 1.0M hydrochloric acid (~9.5 mL). The neutral mixture was heated with stirring to 95–100° C. for 1 h to generate granular reversible cold-water swelling starch with approximately 0.3% phosphorus. The cold-water swelling starch was isolated by washing with water, and drying at 100° C. Alternatively, the swollen/cross-linked wheat starch (ungelatinized) was isolated, purified, and converted to granular, reversible cold-water swelling starch as described in Example 1.

Example 6
Swollen/Cross-Linked Wheat Starch Prepared with Epichlorohydrin and The Instant Form of the Starch Wheat starch was subjected to preswelling for 1 h at 45° C. and pH 11.5 in aqueous sodium hydroxide/sulfate as described in Example 1. Epichlorohydrin (2%, sb) was added, and the mixture was stirred an additional 14 h at 25° C. The slurry was neutralized, and the modified starch purified and dried as before. The product gave 95° C. water-solubility of <1% and swelling power of 7.0 g/g. Heating the product in excess water to 95° C., followed by washing with water and drying at 100° C. gave granular reversible cold-water swellable wheat starch with swelling power at 25 ° C. of 6.9 g/g.

Example 7
Sugar-Snap Cookie

Sugar-snap cookies were prepared according to the "Approved Method of the American Association of Cereal Chemists", Ninth Edition (1995), incorporated by reference; Method 10-52, titled *Baking Quality of Cookie Flour, Micro-Method* (Reviewed 1994). The formula was as follows: cookie flour—40 g (14% mb), sucrose—24 g, shortening—12 g, non-fat dry milk—1.2 g, sodium bicarbonate—0.72 g, ammonium chloride—0.20 g, sodium chloride—0.18 g, and water—8.0 g. The sucrose, non-fat dry milk and about half of the sodium bicarbonate were creamed with the shortening for 3 min. Then a solution (4 mL) containing the remaining sodium bicarbonate, a second solution (2 mL) containing the sodium and ammonium chlorides, and water (2 mL) were mixed 5 min with the creamed ingredients. Finally, the flour was added and the mixing done another 20 sec. The dough was sheeted to 7 mm thickness, cut to 50 mm diameter, and baked 10 min in a preheated oven at 204° C. After cooling, mean cookie diameter and mean thickness of the two cookies were measured.

In the experiment, cookies were made from (A) cookie flour, (B) 3/1 (w/w) mixture of cookie flour and prime wheat starch, (C) a 3/1 (w/w) mixture of cookie flour and cross-linked wheat starch with phosphorus of 0.38% and swelling power of less than 1.5 g/g, and (D) 3/1 (w/w) mixture of cookie flour and swollen-cross-linked wheat starch with phosphorus of 0.28% and swelling power of 6.4 g/g.

TABLE 4

Substitution of 25% Starch for Cookie Flour in Sugar-Snap Cookie

| Treatment | Cookie Diameter (mm) | Cookie Height, Uncorrected (mm) |
|---|---|---|
| A. Cookie flour (blank) | 184, 180 | 14.2, 15.3 |
| B. Cookie flour (3 parts) and prime starch (1 part) (control) | 182, 184 | 13.2, 14.0 |
| C. Cookie flour (3 parts) and cross-linked wheat starch (1 part) | 180, 181 | 15.5, 14.8 |
| D. Cookie flour (3 parts) and swollen/cross-linked wheat starch (1 part) | 177, 180 | 16.2, 15.1 |

The data in Table 4 shows that substituting 25% wheat starch for flour had no effect on cookie diameter but decreased average cookie height by ~8%. Substituting 25% cross-linked wheat starch for flour increased average cookie height 3% compared to the all-flour cookie, while substituting 25% swollen/cross-linked wheat starch increased cookie height 7%. Neither of the cross-linked wheat starches affected cookie diameter nor the surface-crack pattern of the cookie. Thus, there was a tolerable decrease in the spread ratio (width/height) upon adding the swollen/cross-linked wheat starch to a sugar snap cookie, and the cookie appearance was largely unaffected. In addition, cookies C and D contain 13% and 4% resistant starch.

Example 8
Fat-Free Pourable Salad Dressing

Vinegar (10 mL) and granular, reversible cold-water swellable wheat starch (3.5 g) were mixed and warmed to 90° C. for 10 min. Sucrose (5 g) was added with mixing, and then 0.7% zanthan gum or guar gum solution (10 mL) containing garlic powder (50 mg). After shaking vigorously, a thick and stable mixture was formed. The salad dressing remained one phase after three days at 5° C.

We claim:

1. A modified starch comprising a plurality of individual, cross-linked starch granules capable of undergoing multiple cycles of swelling in 95° C. water for a period of 30 minutes followed by drying at 105° C. to a moisture content of less than about 10% by weight, wet basis, while substantially retaining the individuality of said starch granules.

2. The starch of claim 1, wherein said starch granules are selected from the group consisting of cereal, root, tuber, legume and high amylose starches.

3. The starch of claim 2, wherein said starch granules are selected from the group consisting of wheat, corn, waxy corn, high amylose corn, oat, rice, tapioca, mung bean and potato starches.

4. The starch of claim 2, wherein said granules are cross-linked by a crosslinker selected from the group consisting of phosphorylating agents and epichlorohydrin.

5. The starch of claim 4, wherein said crosslinker is selected from the group consisting of sodium trimetaphosphate, sodium tripolyphosphate and mixtures thereof.

6. The starch of claim 5, wherein said starch granules have at least about 0.1% by weight residual phosphorus.

7. The product of claim 1, said starch granules having upon said swelling thereof a swelling power which is at least 100% greater than that of the starch granules after said drying thereof.

8. The starch of claim 7, wherein said swelling power upon said swelling is at least 200% greater than the swelling power of the starch granules after said drying, thereof.

9. The starch of claim 1, wherein there is no more than about 2% by weight starch solubles, based upon the weight of the starting starch, in said water during each of said swellings of said granules.

10. The starch of claim 9, wherein there is no more than about 2% by weight starch solubles in said water during the first of said cycles, and no more than about 1% by weight starch solubles in said water during each of said succeeding cycles, said solubles weights based upon the weight of the starting starch.

11. The starch of claim 1, wherein said starch granules absorb at least about their own weight in water during each of said cycles.

12. The starch of claim 1, wherein said starch granules have at least about 3% resistance to α-amylase digestion using AOAC Method 992.16 (1995).

13. The starch of claim 12, wherein said starch granules have at least about 10% resistance to α-amylase digestion using AOAC Method 992.16 (1995).

14. The starch of claim 1, wherein said starch granules also, after the first of said cycles, undergo multiple cycles of swelling in 25° C. water for a period of 10 minutes followed by drying at 105° C. to a moisture content of less than about 10% by weight, wet basis.

15. A modified starch comprising a plurality of individual, cross-linked starch granules capable of undergoing multiple cycles of swelling in water at 95° C. followed by drying to a moisture content of less than about 10% by weight, wet basis, there being no more than about 2% by weight starch solubles, based upon the weight of the starting starch, in said water during each of said swellings of said granules during said cycles.

16. The starch of claim 15, wherein said starch granules are selected from the group consisting of cereal, root, tuber, legume and high amylose starches.

17. The starch of claim 16, wherein said starch granules are selected from the group consisting of wheat, corn, waxy corn, high amylose corn, oat, rice, tapioca, mung bean and potato starches.

18. The starch of claim 15, wherein said granules are cross-linked by a crosslinker selected from the group consisting of phosphorylating agents and epichlorohydrin.

19. The starch of claim 18, wherein said crosslinker is selected from the group consisting of sodium trimetaphosphate, sodium tripolyphosphate and mixtures thereof.

20. The starch of claim 19, wherein said starch granules have at least about 0.1% by weight residual phosphorus.

21. The starch of claim 15, wherein said starch granules have upon said swelling thereof a swelling power which is at least 100% greater than the swelling power of the starch granules after said drying thereof.

22. The starch of claim 21, wherein said swelling power upon said swelling is at least 200% greater than the swelling power of the starch granules after said drying thereof.

23. The starch of claim 15, wherein there is no more than about 2% by weight starch solubles in said water during the first of said cycles, and no more than about 1% by weight starch solubles in said water during each of said succeeding cycles, said solubles weights based upon the weight of the starting starch.

24. The starch of claim 15, wherein said starch granules absorb at least about their own weight in water during each of said cycles.

25. The starch of claim 15, wherein said starch granules have at least about 3% resistance to α-amylase digestion using AOAC Method 992.16 (1995).

26. The starch of claim 25, wherein said starch granules have at least about 10% resistance to α-amylase digestion using AOAC Method 992.16 (1995).

27. A modified starch comprising a plurality of individual, cross-linked starch granules capable of undergoing multiple cycles of swelling in 95° C. water for a period of 30 minutes followed by drying at 105° C. to a moisture content of less than about 10% by weight, wet basis, said starch granules having upon said swelling thereof during each of said cycles a swelling power which is at least 100% greater than the swelling power of the starch granules after said drying thereof.

28. The starch of claim 27, wherein said starch granules are selected from the group consisting of cereal, root, tuber, legume and high amylose starches.

29. The starch of claim 28, wherein said starch granules are selected from the group consisting of wheat, corn, waxy corn, high amylose corn, oat, rice, tapioca, mung bean and potato starches.

30. The starch of claim 27, wherein said granules are cross-linked by a crosslinker selected from the group consisting of phosphorylating agents and epichlorohydrin.

31. The starch of claim 30, wherein said crosslinker is selected from the group consisting of sodium trimetaphosphate, sodium tripolyphosphate and mixtures thereof.

32. The starch of claim 31, wherein said starch granules have at least about 0.1% by weight residual phosphorus.

33. The starch of claim 29, wherein said swelling power upon said swelling is at least 200% greater than the swelling power of the starch granules after said drying thereof.

34. The starch of claim 29, wherein there is no more than about 2% by weight starch solubles, based upon the weight of the starting starch, in said water during each of said swellings of said granules.

35. The starch of claim 34, wherein there is no more than about 2% by weight starch solubles in said water during the first of said cycles, and no more than about 1% by weight starch solubles in said water during each of said succeeding cycles, said solubles weights based upon the weight of the starting starch.

36. The starch of claim 27, wherein said starch granules absorb at least about their own weight in water during each of said cycles.

37. The starch of claim 27, wherein said starch granules have at least about 3% resistance to α-amylase digestion using AOAC Method 992.16 (1995).

38. The starch of claim 37, wherein said starch granules have at least about 10% resistance to α-amylase digestion using AOAC Method 992.16 (1995).

39. A method of preparing a starch comprising the steps of:
   forming a dispersion of starch granules in water, said granules undergoing swelling in said dispersion and having a crystalline phase;
   adding a cross-linking agent to said dispersion while said granules are swelled and cross-linking the swelled starch granules under conditions of continued swelling, said cross-linking step being carried out without complete gelatinization of said swelled starch granules; and
   heating said cross-linked starch granules in excess water in order to melt the crystalline phase of said granules.

40. The method of claim 39, including the steps of first forming a dispersion of starch granules in an aqueous system, and heating said dispersion in order to preswell said granules prior to said addition of said cross-linking agent, said preswelling and cross-linking steps being carried out without complete gelatinization of said starch granules.

41. The method of claim 39, wherein said starch granules are selected from the group consisting of cereal, root, tuber, legume and high amylose starches.

42. The method of claim 41, wherein said starch granules are selected from the group consisting of wheat, corn, waxy corn, high amylose corn, oat, rice, tapioca, mung bean and potato starches.

43. The method of claim 39, wherein said cross-linking agent is selected from the group consisting of phosphorylating agents and epichlorohydrin.

44. The method of claim 43, wherein said cross-linking agent is selected from the group consisting of sodium trimetaphosphate, sodium tripolyphosphate and mixtures thereof.

45. The method of claim 44, wherein said crosslinked starch granules have at least about 0.1% by weight residual phosphorus.

46. The method of claim 40, wherein said system also includes a base and a salt therein.

47. The method of claim 46, wherein said base is selected from the group consisting of the alkali metal hydroxides, said salt being selected from the group consisting of the alkali metal and alkaline earth metal chlorides, sulfates and carbonates.

48. The method of claim 47, wherein said alkali metal hydroxide is present at a level of from about 1 to 3% by weight of starch in said dispersion, said salt being present at a level of from about 5 to 25% by weight of starch in said dispersion.

49. The method of claim 40, wherein said dispersion is heated for a period of from about 0.1–3 hours.

50. The method of claim 49, wherein said period is from about 0.5–1 hour.

51. The method of claim 40, wherein said dispersion is heated to a temperature of from about 30 to 75° C.

52. The method of claim 39, wherein said dispersion has from about 20–40% by weight starch solids therein.

53. The method of claim 39, comprising the steps of boiling said crosslinked starch granules.

54. The method of claim 53, including the step of boiling said crosslinked starch granules for at least about 5 minutes.

55. The method of claim 53, including the step of cooling the boiled crosslinked starch granules, and removing water therefrom.

56. A thickener composition comprising quantities of gum and the starch of claim 1.

57. The thickener composition of claim 56, wherein said starch is present at a level of from about 5–15% by weight.

58. The thickener composition of claim 56, wherein said gum is present at a level of from about 0.03–1% by weight.

59. The thickener composition of claim 56, wherein said gum is selected from the group consisting of guar, xanthan, karaya, acacia, and tragacanth gums.

60. A food product including therein the starch of claim 1.

61. The food product of claim 60, wherein the food product is selected from the group consisting of leavened or unleavened, baked or fried cereal grain-containing foods and salad dressings.

62. A cosmetic or personal care product including therein the starch of claim 1.

\* \* \* \* \*